United States Patent [19]
Wariishi et al.

[11] Patent Number: 5,543,529
[45] Date of Patent: Aug. 6, 1996

[54] 1-CARBAMOYL-5-HYDROXYPYRAZOLE COMPOUNDS AND SALTS THEREOF

[75] Inventors: Koji Wariishi; Mario Aoki, both of Kanagawa, Japan

[73] Assignee: Fuji Photo Film Co., Ltd., Kanagawa, Japan

[21] Appl. No.: 378,403

[22] Filed: Jan. 26, 1995

[30] Foreign Application Priority Data

Jan. 27, 1994 [JP] Japan .................... 6-007761

[51] Int. Cl.$^6$ .............. C07D 231/18; C07D 231/14
[52] U.S. Cl. ................ 548/366.7; 548/368.4; 548/367.9; 548/369.7; 548/364.1; 544/140; 546/211
[58] Field of Search ............ 548/366.7, 368.4, 548/369.7, 367.7

[56] References Cited

U.S. PATENT DOCUMENTS

| | | | |
|---|---|---|---|
| Re. 34,779 | 11/1994 | Oya et al. | 504/282 |
| 2,274,782 | 3/1942 | Gaspar | 95/2 |
| 4,316,040 | 2/1982 | Plath et al. | 548/377 |

FOREIGN PATENT DOCUMENTS

| | | | |
|---|---|---|---|
| 5177323 | 5/1976 | Japan | H04R 7/04 |
| 54-118247 | 9/1979 | Japan | C09B 57/00 |
| 3288841 | 12/1991 | Japan | G03C 1/06 |
| 48466 | 2/1992 | Japan | C09B 23/00 |

Primary Examiner—Johann Richter
Assistant Examiner—Laura L. Stockton
Attorney, Agent, or Firm—Sughrue, Mion, Zinn, Macpeak & Seas

[57] ABSTRACT

Pyrazole compounds represented by formulae (A), (B), and (C):

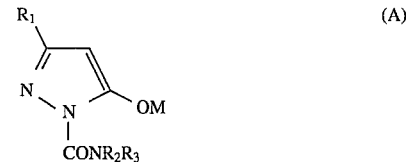

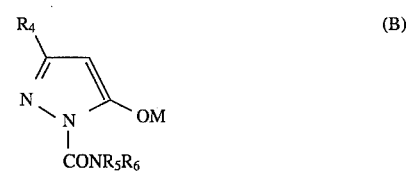

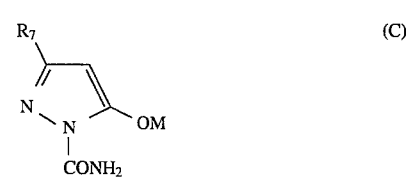

wherein $R_1$ represents an unsubstituted alkyl group, an ester group, a carboxyl group, an amino group or an aryl group; $R_2$ and $R_3$ each represents an alkyl group or an aryl group, and the alkyl groups represented by $R_2$ and $R_3$ may bond each other to form a saturated 5- or 6-membered ring; $R_4$ represents an alkoxy group or a carbonamido group; $R_5$ and $R_6$ each represents a hydrogen atom, an alkyl group or an aryl group, and the alkyl groups represented by $R_5$ and $R_6$ may bond each other to form a saturated 5- or 6-membered ring; $R_7$ represents an aryl group, an ester group or a carboxyl group; and M represents a hydrogen atom or a monovalent cation.

16 Claims, No Drawings

1-CARBAMOYL-5-HYDROXYPYRAZOLE COMPOUNDS AND SALTS THEREOF

FIELD OF THE INVENTION

The present invention relates to novel pyrazole compounds respectively represented by formulae (A) to (C), which compounds are useful, e.g., as a dye intermediate.

BACKGROUND OF THE INVENTION

1-Substituted 5-hydroxypyrazoles are useful as an intermediate for a dye as described in "Riron/Seizō- Senryō Kagaku (Theory/Production - Dye Chemistry)" written by Yutaka Hosoda (published by Gihōdo in 1957). Dyes produced from these 1-substituted 5-hydroxypyrazoles as intermediates are useful in silver halide photographic materials for regulating spectral sensitivity or preventing irradiation and halation. Examples of such dyes developed so far are described, e.g., in U.S. Pat. No. 2,274,782, JP-A-51-77323, JP-A-54-118247, JP-A-3-288841, and JP-B-4-8466. (The terms "JP-A" and "JP-B" as used herein mean an "unexamined published Japanese patent application" and an "examined Japanese patent publication," respectively.) However, the dyes produced from those conventional pyrazole derivative intermediates have problems, for example, that an absorption spectrum sufficiently suited for the intended use cannot be obtained because the dyes, for example, has a large side absorption or have a too broad absorption region.

SUMMARY OF THE INVENTION

Accordingly, an object of the present invention is to provide novel pyrazole compounds useful as an intermediate for a dye having a sharp absorption peak which has a few side absorption.

The above object is accomplished with compounds respectively represented by formulae (A), (B), and (C):

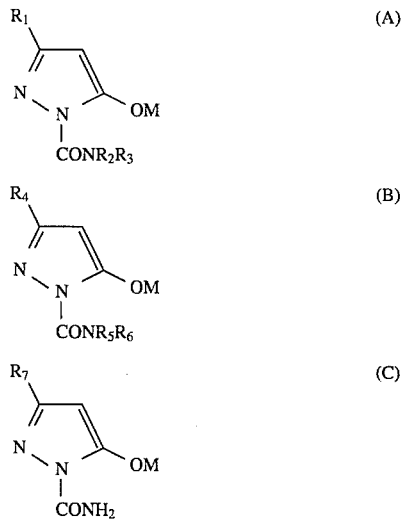

wherein $R_1$ represents an unsubstituted alkyl group, an ester group, a carboxyl group, an amino group or an aryl group; $R_2$ and $R_3$ each represents an alkyl group or an aryl group, and the alkyl groups represented by $R_2$ and $R_3$ may bond to each other to form a saturated 5- or 6-membered ring; $R_4$ represents an alkoxy group or a carbonamido group; $R_5$ and $R_6$ each represents a hydrogen atom, an alkyl group or an aryl group, and the alkyl groups represented by $R_5$ and $R_6$ may bond each other to form a saturated 5- or 6-membered ring; $R_7$ represents an aryl group, an ester group or a carboxyl group; and M represents a hydrogen atom or a monovalent cation.

DETAILED DESCRIPTION OF THE INVENTION

Formula (A) is explained below in detail.

The alkyl group represented by $R_1$ is a linear, branched, or cyclic alkyl group which has no substituent. Examples thereof include methyl, ethyl, n-propyl, n-butyl, sec-butyl, t-butyl, isobutyl, n-pentyl, n-hexyl, cyclohexyl, 2-ethylhexyl, and cyclopentyl. The alkyl group desirably has 1 to 10 carbon atoms, and preferably is a linear or branched alkyl group having 1 to 10 carbon atoms.

The ester group represented by $R_1$ is desirably a group having a saturated alkoxy group. Examples thereof include methoxycarbonyl, ethoxycarbonyl, and isopropoxycarbonyl. The ester group is preferably a group having a saturated alkoxy group having up to 7 carbon atoms.

The amino group represented by $R_1$ may have a substituent. The substituent is desirably an alkyl group or an aryl group, preferably an alkyl group. Examples of the substituent include alkyl groups having 1 to 8 carbon atoms (e.g., methyl, ethyl, isopropyl and n-butyl), and aryl groups having 6 to 10 carbon atoms having 6 to 10 carbon atoms (e.g., phenyl and naphthyl).

The aryl group represented by $R_1$ is desirably an aryl group having 6 to 10 carbon atoms (e.g., phenyl and naphthyl), preferably a phenyl group, and may have a substituent. Examples of the substituent include alkyl groups having 1 to 4 carbon atoms (e.g., methyl, ethyl, t-butyl, and n-propyl), halogen atoms (e.g., F, Cl, and Br), a cyano group, alkoxy groups having 1 to 8 carbon atoms (e.g., methoxy and ethoxy), alkylthio groups having 1 to 8 carbon atoms (e.g., methylthio and ethylthio), a carboxyl group, ester groups having 2 to 8 carbon atoms (e.g., methoxycarbonyl and ethoxycarbonyl), carbamoyl groups having 1 to 8 carbon atoms (e.g., dimethylcarbamoyl and diethylcarbamoyl), alkanesulfonyl groups having 1 to 8 carbon atoms (e.g., methanesulfonyl), carbonamido groups having 2 to 8 carbon atoms (e.g., acetylamino and n-propionylamino), acyl groups having 2 to 8 carbon atoms (e.g., acetyl and propionyl), urethane groups having 2 to 8 carbon atoms (e.g., methoxycarbonylamino and n-butoxycarbonylamino), ureide groups having 1 to 8 carbon atoms (e.g., methylcarbamoylamino and phenylcarbamoylamino), sulfamoyl groups having 0 to 8 carbon atoms (e.g., methylsulfamoyl and ethylsulfamoyl), a sulfo group, a hydroxyl group, and substituted amino groups such as dimethylamino.

Examples of the alkyl group represented by $R_2$ or $R_3$ include the alkyl groups enumerated above as examples of $R_1$. The alkyl group represented by $R_2$ or $R_3$ may have a substituent. Examples of the substituent include a hydroxyl group, alkoxy groups having 1 to 8 carbon atoms (e.g., methoxy and ethoxy), ester groups having 2 to 8 carbon atoms (e.g., methoxycarbonyl and ethoxycarbonyl), carbamoyl groups having 1 to 8 carbon atoms (e.g., dimethylcarbamoyl and diethylcarbamoyl), a sulfo group, sulfamoyl groups having 0 to 8 carbon atoms (e.g., methylsulfamoyl and ethylsulfamoyl), and a cyano group.

The substituted or unsubstituted alkyl groups respectively represented by $R_2$ and $R_3$ may bond to each other to form a 5- or 6-membered saturated ring. Examples of this ring include a morpholine ring, a piperidine ring, and a pyrrolidine ring.

The aryl group represented by $R_2$ or $R_3$ has the same meaning as the aryl group represented by $R_1$.

The compound represented by formula (A) is preferably one in which $R_1$ is an unsubstituted alkyl group having up to 10 carbon atoms, an ester group having up to 7 carbon atoms, a carboxyl group, an amino group, or an unsubstituted or substituted phenyl group and $R_2$ and $R_3$ each is an alkyl group having up to 10 carbon atoms or an unsubstituted or substituted phenyl group. Especially preferably, the compound represented by general formula (A) is one in which $R_1$ is an unsubstituted alkyl group having up to 4 carbon atoms, an ethoxycarbonyl group, a carboxyl group, an amino group, or an unsubstituted phenyl group and $R_2$ and $R_3$ each is an alkyl group having up to 4 carbon atoms or an unsubstituted phenyl group.

Examples of the carbonamido group represented by $R_4$ include acetylamino, propionylamino, valerylamino, and benzoylamino. The carbonamido group preferably has 2 to 8 carbon atoms.

Examples of the alkoxy group represented by $R_4$ include methoxy and ethoxy. The alkoxy group preferably has 1 to 8 carbon atoms.

The alkyl or aryl group represented by $R_5$ or $R_6$ has the same meaning as the alkyl or aryl group represented by $R_2$ or $R_3$.

The compound represented by formula (B) is preferably one in which $R_4$ is an alkoxy group having up to 8 carbon atoms or a carbonamido group having up to 8 carbon atoms and $R_5$ and $R_6$ each is a hydrogen atom, an alkyl group having up to 10 carbon atoms, or an unsubstituted or substituted phenyl group. Especially preferably, the compound represented by formula (B) is one in which $R_4$ is an alkoxy group having up to 2 carbon atoms or a carbonamido group having up to 6 carbon atoms and $R_5$ and $R_6$ each is a hydrogen atom, an alkyl group having up to 4 carbon atoms, or an unsubstituted phenyl group.

The aryl group and ester group represented by $R_7$ respectively have the same meanings as the aryl group and ester group represented by $R_1$.

Preferred examples of the substituent of $R_7$ include unsubstituted or substituted phenyl groups, ester groups having up to 7 carbon atoms, and a carboxyl group.

Examples of the monovalent cation represented by M include ions of alkali metals, e.g., sodium and potassium, ammonium, lower alkylammoniums, e.g., triethylammonium, and pyridinium (including substituted pyridiniums).

Specific examples of the pyrazole compounds of the present invention are given below.

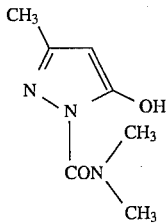
1.

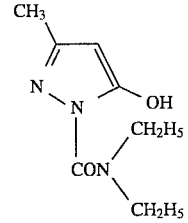
2.

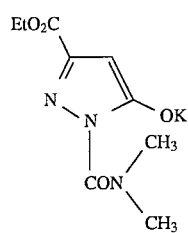
3.

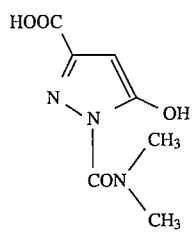
4.

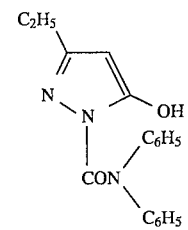
5.

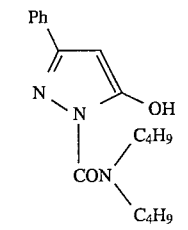
6.

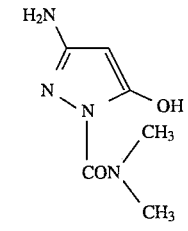
7.

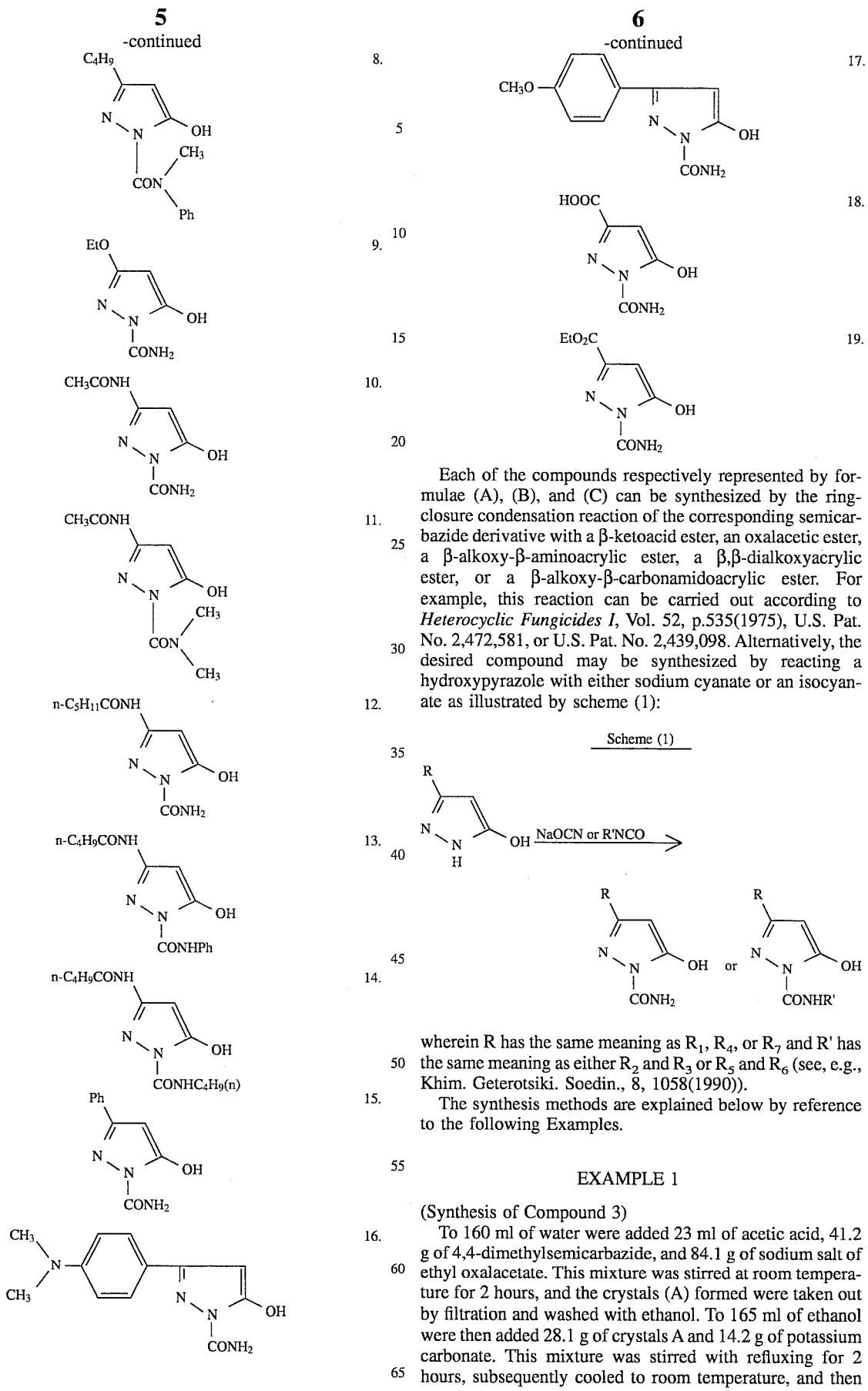

Each of the compounds respectively represented by formulae (A), (B), and (C) can be synthesized by the ring-closure condensation reaction of the corresponding semicarbazide derivative with a β-ketoacid ester, an oxalacetic ester, a β-alkoxy-β-aminoacrylic ester, a β,β-dialkoxyacrylic ester, or a β-alkoxy-β-carbonamidoacrylic ester. For example, this reaction can be carried out according to *Heterocyclic Fungicides I*, Vol. 52, p.535(1975), U.S. Pat. No. 2,472,581, or U.S. Pat. No. 2,439,098. Alternatively, the desired compound may be synthesized by reacting a hydroxypyrazole with either sodium cyanate or an isocyanate as illustrated by scheme (1):

Scheme (1)

wherein R has the same meaning as $R_1$, $R_4$, or $R_7$ and R' has the same meaning as either $R_2$ and $R_3$ or $R_5$ and $R_6$ (see, e.g., Khim. Geterotsiki. Soedin., 8, 1058(1990)).

The synthesis methods are explained below by reference to the following Examples.

EXAMPLE 1

(Synthesis of Compound 3)

To 160 ml of water were added 23 ml of acetic acid, 41.2 g of 4,4-dimethylsemicarbazide, and 84.1 g of sodium salt of ethyl oxalacetate. This mixture was stirred at room temperature for 2 hours, and the crystals (A) formed were taken out by filtration and washed with ethanol. To 165 ml of ethanol were then added 28.1 g of crystals A and 14.2 g of potassium carbonate. This mixture was stirred with refluxing for 2 hours, subsequently cooled to room temperature, and then filtered through a Celite. The ethanol was distilled off the filtrate to obtain 14.9 g of the desired compound as an oily substance.

Chemical shift δ in $^1$H NMR:
1.264.(3H, t)
2.98 (6H, bs)
4.21 (2H, q)
5.3 (1H, bs)

EXAMPLE 2

(Synthesis of Compound 4)

To 110 ml of water was added 37.3 g of Compound 3. This solution was cooled to 0° C. Thereto was carefully added 13.9 g of potassium hydroxide so that the temperature of the resulting mixture was kept at 10° C. or lower. Thereafter, the mixture was stirred at 0° C. for 2 hours. The resulting reaction mixture was neutralized with 35 ml of concentrated hydrochloric acid, and the crystals precipitated were taken out by filtration. Thus, 17.2 g of the desired compound was obtained, which had a melting point of 185° C. (decomposed).

EXAMPLE 3

(Synthesis of Compound 12)

In 60 ml of acetic acid was suspended 10.0 g of 3-hexanoylamino- 5-hydroxypyrazole. This suspension was cooled on a water bath, and a solution of 4.7 g of sodium cyanate in 40 ml of $H_2O$ was added thereto dropwise. After completion of the addition, the mixture was stirred at room temperature for 3 hours, and the crystals formed were taken out by filtration and washed with water. Thus, 8.0 g of the desired compound was obtained, which had a melting point of 164° C. (decomposed).

EXAMPLE 4

(Synthesis of Compound 19)

To 200 ml of water were added 22.3 g of semicarbazide hydrochloride and 42.0 g of sodium salt of ethyl oxalacetate. This mixture was stirred at room temperature for 2 hours, and the crystals (B) formed were taken out by filtration and washed with water. To 150 ml of ethanol were then added 31 g of crystals (B) and 17.5 g of potassium carbonate. This mixture was stirred with refluxing for 2 hours, subsequently cooled to room temperature, and then filtered through a Celite. The ethanol was distilled off the filtrate, and 100 ml of $H_2O$ was added to the residue. This aqueous solution was neutralized with concentrated hydrochloric acid, and the crystals formed were taken out by filtration and washed with water. Thus, 11 g of the desired compound was obtained, which had a melting point of 154° C. (decomposed).

REFERENCE EXAMPLE (Synthesis of Dye)

With 40 ml of ethanol were mixed 4.5 g of Compound 3 and 2.3 g of malonaldehyde dianil hydrochloride. Thereto was added 2.8 ml of triethylamine. This mixture was stirred at 60° C. for 4 hours, and then cooled to room temperature. Subsequently, 2.0 g of potassium acetate was added, and the resulting mixture was filtered. To the filtrate were added 25 ml of isopropyl alcohol and 25 ml of ethyl acetate. The resulting solid was taken out by filtration to obtain dye A in an amount of 1.4 g.

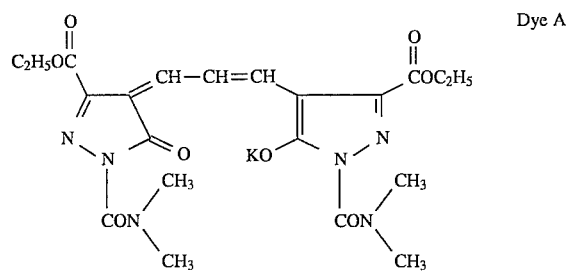

Dye A

Absorption characteristics of Dye A and of Comparative Dye B are shown in Table 1.

TABLE 1

| Compound | $\lambda_{max}$ (in water) | Half band width | Intensity of side absorption* |
| --- | --- | --- | --- |
| Dye A | 543 nm | 53 nm | 0.06 |
| Comparative Dye B | 551 nm | 60 nm | 0.085 |

*Absorbance of each dye at 400 nm when the absorbance at $\lambda_{max}$ is 1.

Comparative Dye B

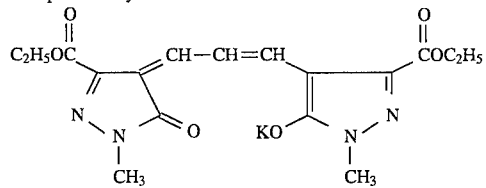

Table 1 shows that the dye obtained from a pyrazole compound of the present invention has a sharp absorption peak with reduced side absorption as compound with the conventional dye.

According to the present invention, pyrazole compounds useful, e.g., as an intermediate for a dye having excellent absorption characteristics can be provided.

While the invention has been described in detail and with reference to specific embodiments thereof, it will be apparent to one skilled in the art that various changes and modifications can be made wherein without departing from the spirit and scope thereof.

What is claimed is:

1. A pyrazole compound represented by formula (A)

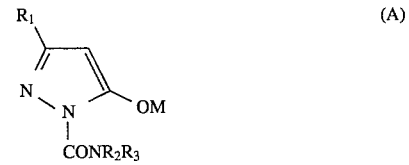

(A)

wherein $R_1$ represents an unsubstituted alkyl group, an ester group, a carboxyl group, a substituted or unsubstituted amino group or a substituted or unsubstitued aryl group; $R_2$ and $R_3$ each represents a substituted or unsubstituted alkyl group or a substituted or unsubstituted aryl group, and the alkyl groups represented by $R_2$ and $R_3$ may bond to each other to form a 5- or 6-membered saturated ring; and M represents a hydrogen atom or a monovalent cation.

2. A pyrazole compound as claimed in claim 1, wherein
(i) $R_1$ represents
an unsubstituted alkyl group having 1 to 10 carbon atoms,
an ester group having up to 7 carbon atoms,
a carboxyl group,
an amino group which may have a substituent selected from the group consisting of an alkyl group having 1 to 8 carbon atoms and an aryl group having 6 to 10 carbon atoms, or an aryl group which may have a substituent selected from the group consisting of an alkyl group having 1 to 4 carbon atoms, a halogen atom, a cyano group, an alkoxy group having 1 to 8 carbon atoms, an alkylthio group having 1 to 8 carbon atoms, a carboxyl group, an ester group having 2 to 8 carbon atoms, a carbamoyl group having 1 to 8 carbon atoms, an alkylsulfonyl group having 1 to 8 carbon atoms, a carbonamido group having 2 to 8 carbon atoms, an acyl group having 2 to 8 carbon atoms, an urethane group having 2 to 8 carbon atoms, an ureide group having 1 to 8 carbon atoms, a sulfamoyl group having 0 to 8 carbon atoms, a sulfo group, a hydroxyl group and a dimethylamino group, the aryl group having 6 to 10 carbon atoms exclusive of the substituent, (ii) $R_2$ and $R_3$ each represents an alkyl group which may have a substituent selected from the group consisting of a hydroxyl group, an alkoxy group having 1 to 8 carbon atoms, an ester group having 2 to 8 carbon atoms, a carbamoyl group having 1 to 8 carbon atoms, a sulfo group, a sulfamoyl group having 0 to 8 carbon atoms and a cyano group, the alkyl group having 1 to 10 carbon atoms exclusive of the substituent, or an aryl group which may have a substituent selected from the group consisting of an alkyl group having 1 to 4 carbon atoms, a halogen atom, a cyano group, an alkoxy group having 1 to 8 carbon atoms, an alkylthio group having 1 to 8 carbon atoms, a carboxyl group, an ester group having 2 to 8 carbon atoms, a carbamoyl group having 1 to 8 carbon atoms, an alkylsulfonyl group having 1 to 8 carbon atoms, a carbonamido group having 2 to 8 carbon atoms, an acyl group having 2 to 8 carbon atoms, an urethane group having 2 to 8 carbon atoms, an ureide group having 1 to 8 carbon atoms, a sulfamoyl group having 0 to 8 carbon atoms, a sulfo group, a hydroxyl group and a dimethylamino group, the aryl group having 6 to 10 carbon atoms exclusive of the substituent, and the alkyl groups represented by $R_2$ and $R_3$ may bond to each other to form a 5- or 6-membered saturated ring; and (iii) M represents a hydrogen atom or a monovalent cation.

3. A pyrazole compound as claimed in claim 2, wherein $R_1$ represents methyl, ethyl, n-propyl, n-butyl, sec-butyl, t-butyl, isobutyl, n-pentyl, n-hexyl, cyclohexyl, 2-ethylhexyl, cyclopentyl, methoxycarbonyl, ethoxycarbonyl, isopropoxycarbonyl, a carbonyl group, an amino group which may have a substituent selected from the group consisting of methyl, ethyl, isopropyl, n-butyl, phenyl and naphthyl, or a phenyl or naphthyl group which may have a substituent selected from the group consisting of methyl, ethyl, t-butyl, n-propyl, F, Cl, Br, a cyano group, methoxy, ethoxy, methylthio, ethylthio, a carboxyl group, methoxycarbonyl, ethoxycarbonyl, dimethylcarbamoyl, diethylcarbamoyl, methanesulfonyl, acetylamino, propionylamino, an acetyl group, a propionyl group, methoxycarbonylamino, n-butoxycarbonylamino, methylcarbamoylamino, phenylcarbamoylamino, methylsulfamoyl, ethylsulfamoyl, a sulfo group, a hydroxyl group and a dimethylamino group; and $R_2$ and $R_3$ each represents methyl, ethyl, n-propyl, n-butyl, sec-butyl, t-butyl, isobutyl, n-pentyl, n-hexyl, cyclohexyl, 2-ethylhexyl, cyclopentyl, an alkyl group having a substituent selected from the group consisting of a hydroxyl group, methoxy, ethoxy, methoxycarbonyl, ethoxycarbonyl, dimethylcarbomoyl, diethylcarbamoyl, a sulfo group, methylsulfamoyl, ethylsulfamoyl and a cyano group, or a phenyl or naphthyl group which may have a substituent selected from the group consisting of methyl, ethyl, t-butyl, n-propyl, F, Cl, Br, cyano, methoxy, ethoxy, methylthio, ethylthio, carboxyl, methoxycarbonyl, ethoxycarbonyl, dimethylcarbamoyl, diethylcarbamoyl, methanesulfonyl, acetylamino, propionylamino, acetyl, propionyl, methoxycarbonylamino, n-butoxycarbonylamino, methylcarbamoylamino, phenylcarbamoylamino, methylsulfamoyl, ethylsulfamoyl, sulfo, hydroxyl and dimethylamino, or said 5- or 6-membered ring formed by $R_2$ and $R_3$ is a morpholine ring, a piperidine ring or a pyrrolidine ring.

4. A pyrazole compound as claimed in claim 2, wherein $R_1$ represents an unsubstituted alkyl group having 1 to 10 carbon atoms, an ester group having up to 7 carbon atoms, a carboxyl group, an amino group or a phenyl group; and $R_2$ and $R_3$ each represents an alkyl group having 1 to 10 carbon atoms or a phenyl group.

5. A pyrazole compound as claimed in claim 2, wherein $R_1$ represents an unsubstituted alkyl group having 1 to 4 carbon atoms, an ethoxycarbonyl group, a carboxyl group, an amino group or an unsubstituted phenyl group, and $R_2$ and $R_3$ each represents an alkyl group having 1 to 4 carbon atoms or an unsubstituted phenyl group.

6. A pyrazole compound represented by formula (B)

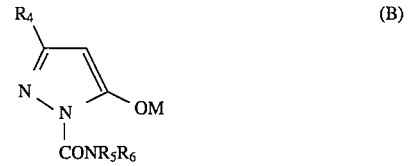

(B)

wherein $R_4$ represents an alkoxy group or a carbonamido group; $R_5$ and $R_6$ each represents a hydrogen atom, a substituted or unsubstituted alkyl group or a substituted or unsubstituted aryl group, and the alkyl groups represented by $R_5$ and $R_6$ may bond to each other to form a 5- or 6-membered saturated ring; and M represents a hydrogen atom or a monovalent cation.

7. A pyrazole compound as claimed in claim 6, wherein (i) $R_4$ represents an alkoxy group having 1 to 8 carbon atoms or a carbonamido group having 2 to 8 carbon atoms;

(ii) $R_5$ and $R_6$ each represents a hydrogen atom, an alkyl group which may have a substituent selected from the group consisting of a hydroxyl group, an alkoxy group having 1 to 8 carbon atoms, an ester group having 2 to 8 carbon atoms, a carbamoyl group having 1 to 8 carbon atoms, a sulfo group, a sulfamoyl group having 0 to 8 carbon atoms and a cyano group, the alkyl group having 1 to 10 carbon atoms exclusive of the substituent, or an aryl group which may have a substituent selected from the group consisting of an alkyl group having 1 to 4 carbon atoms, a halogen atom, a cyano group, an alkoxy group having 1 to 8 carbon atoms, an alkylthio group having 1 to 8 carbon atoms, a carboxyl group, an ester group having 2 to 8 carbon atoms, a carbamoyl group having 1 to 8 carbon atoms, an alkylsulfonyl group having 1 to 8 carbon atoms, a carbonamido group having 2 to 8 carbon atoms, an acyl group having 2 to 8 carbon atoms, an urethane group having 2 to 8 carbon atoms, an ureide group having 1 to 8 carbon atoms, a sulfamoyl group having 0 to 8 carbon atoms, a sulfo group, a hydroxyl group and a dimethylamino group, the aryl group having 6 to 10 carbon atoms exclusive of the substituent, and the alkyl groups represented by $R_5$ and $R_6$ may bond to each other to form a 5- or 6-membered saturated ring; and (iii) M represents a hydrogen atom or a monovalent cation.

8. A pyrazole compound as claimed in claim 7, wherein $R_4$ represents methoxy, ethoxy, acetylamino, n-propionylamino, valerylamino or benzoylamino; and $R_5$ and $R_6$ each represents a hydrogen atom, methyl, ethyl, propyl, n-butyl, sec-butyl, t-butyl, isobutyl, n-pentyl, n-hexyl, cyclohexyl, 2-ethylhexyl, cyclopentyl, an alkyl group having a substituent selected from the group consisting of a hydroxyl group, methoxy, ethoxy, methoxycarbonyl, ethoxycarbonyl, dimethylcarbomoyl, diethylcarbamoyl, a sulfo group, methylsulfamoyl, ethylsulfamoyl and a cyano group, a phenyl or naphthyl group which may have a substituent selected from the group consisting of methyl, ethyl, t-butyl, n-propyl, F, Cl, Br, cyano, methoxy, ethoxy, methylthio, ethylthio, carboxyl, methoxycarbonyl, ethoxycarbonyl, dimethylcarbamoyl, diethylcarbamoyl, methanesulfonyl, acetylamino, propionylamino, acetyl, propionyl, methoxycarbonylamino, n-butoxycarbonylamino, methylcarbamoylamino, phenylcarbamoylamino, methylsulfamoyl, ethylsulfamoyl, sulfo, hydroxyl and dimethylamino, or said 5- or 6-membered ring formed by $R_5$ and $R_6$ is a morpholine ring, a piperidine ring or a pyrrolidine ring.

9. A pyrazole compound as claimed in claim 7, wherein $R_4$ represents an alkoxy group having 1 to 8 carbon atoms, a carbonamido group having 2 to 8 carbon atoms, and $R_5$ and $R_6$ each represents a hydrogen atom, an alkyl group having 1 to 10 carbon atoms or a phenyl group.

10. A pyrazole compound as claimed in claim 7, wherein $R_4$ represents an alkoxy group having 1 or 2 carbon atoms, a carbonamido group having 2 to 6 carbon atoms, and $R_5$ and $R_6$ each represents a hydrogen atom, an alkyl group having 1 to 4 carbon atoms or an unsubstituted phenyl group.

11. A pyrazole compound represented by formula (C)

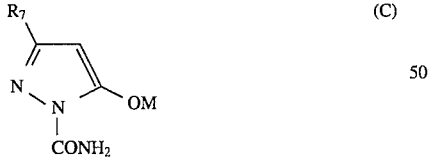

wherein $R_7$ represents a substituted or unsubstituted aryl group, an ester group, or a carboxyl group; and M represents a hydrogen atom or a monovalent cation.

12. A pyrazole compound as claimed in claim 11, wherein (i) $R_7$ represents
an aryl group which may have a substituent selected from the group consisting of an alkyl group having 1 to 4 carbon atoms, a halogen atom, a cyano group, an alkoxy group having 1 to 8 carbon atoms, an alkylthio group having 1 to 8 carbon atoms, a carboxyl group, an ester group having 2 to 8 carbon atoms, a carbamoyl group having 1 to 8 carbon atoms, an alkylsulfonyl group having 1 to 8 carbon atoms, a carbonamido group having 2 to 8 carbon atoms, an acyl group having 2 to 8 carbon atoms, an urethane group having 2 to 8 carbon atoms, an ureide group having 1 to 8 carbon atoms, a sulfamoyl group having 0 to 8 carbon atoms, a sulfo group, a hydroxyl group and a dimethylamino group, the aryl group having 6 to 10 carbon atoms exclusive of the substituent, an ester group having up to 7 carbon atoms, and
a carboxyl group; and (ii) M represents a hydrogen or a monovalent cation.

13. A pyrazole compound as claimed in claim 12, wherein $R_7$ represents a phenyl or naphthyl group which may have a substituent selected from the group consisting of methyl, ethyl, t-butyl, n-propyl, F, Cl, Br, a cyano group, methoxy, ethoxy, methylthio, ethylthio, a carboxyl group, methoxycarbonyl, ethoxycarbonyl, dimethylcarbamoyl, diethylcarbamoyl, methanesulfonyl, acetylamino, propionylamino, an acetyl group, a propionyl group, methoxycarbonylamino, n-butoxycarbonylamino, methylcarbamoylamino, phenylcarbamoylamino, methylsulfamoyl, ethylsulfamoyl, a sulfo group, a hydroxyl group and a dimethylamino group; methoxycarbonyl; ethoxycarbonyl; isopropylcarbonyl; or a carboxyl group.

14. A pyrazole compound as claimed in claim 12, wherein $R_7$ represents a phenyl group, an ester group having up to 7 carbon atoms or a carboxyl group.

15. A pyrazole compound represented by formula (A)

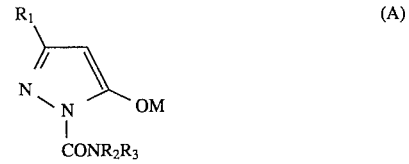

wherein $R_1$ represents an unsubstituted alkyl group, an ester group, a carboxyl group, an amino group or an aryl group; $R_2$ and $R_3$ each represents an alkyl group or an aryl group and M represents a hydrogen atom or a monovalent cation.

16. A pyrazole compound represented by formula (B)

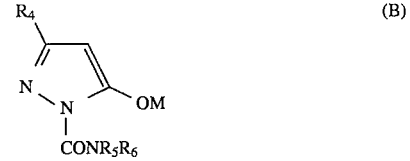

wherein $R_4$ represents an alkoxy group or a carbonamido group; $R_5$ and $R_6$ each represents a hydrogen atom, an alkyl group or an aryl group and M represents a hydrogen atom or a monovalent cation.

* * * * *